US012148153B2

(12) United States Patent
Zhu et al.

(10) Patent No.: US 12,148,153 B2
(45) Date of Patent: Nov. 19, 2024

(54) SYSTEM AND METHOD TO DETECT ABNORMALITY OF SUBJECTS DIRECTLY FROM MRI K-SPACE DATA

(71) Applicant: CHENGDU YIJIAN MEDICAL TECHNOLOGY CO., LTD, Chengdu (CN)

(72) Inventors: Ruixing Zhu, Chengdu (CN); Zhizun Zhang, Chengdu (CN); Hangxuan Li, Chengdu (CN)

(73) Assignee: HANGZHOU WEIYING MEDICAL TECHNOLOGY CO., LTD., Hangzhou (CN)

(*) Notice: Subject to any disclaimer, the term of this patent is extended or adjusted under 35 U.S.C. 154(b) by 435 days.

(21) Appl. No.: 17/513,911

(22) Filed: Oct. 29, 2021

(65) Prior Publication Data
US 2022/0138943 A1 May 5, 2022

Related U.S. Application Data

(60) Provisional application No. 63/107,458, filed on Oct. 30, 2020.

(51) Int. Cl.
G06T 7/00 (2017.01)
G01R 33/483 (2006.01)
(Continued)

(52) U.S. Cl.
CPC ........ G06T 7/0012 (2013.01); G01R 33/4836 (2013.01); G01R 33/56 (2013.01);
(Continued)

(58) Field of Classification Search
CPC ............... G06T 7/0012; G06T 2200/04; G06T 2207/10088; G06T 2207/20081;
(Continued)

(56) References Cited

U.S. PATENT DOCUMENTS 9,339,239 B2 * 5/2016 Wang .................... A61B 5/7221
2009/0128553 A1 * 5/2009 Perry ..................... A61B 5/055
345/419

(Continued)

FOREIGN PATENT DOCUMENTS

JP 2017131663 A * 8/2017

Primary Examiner — Ping Y Hsieh
Assistant Examiner — Xiao Liu

(57) ABSTRACT

A system and method to detect abnormality of subjects directly from MRI k-space data are provided. The system includes: at least one computer hardware processor, at least one non-transitory computer-readable storage medium, and at least one computer program stored in the at least one non-transitory computer-readable storage medium and executable on the at least one computer hardware processor, wherein the at least one computer program includes: an acquisition module, configured to obtain target MRI k-space data by scanning a subject, wherein the target MRI k-space data are fully-sampled or undersampled or sparse MRI k-space data; a detection module, configured to obtain and output detection outcome from the target MRI k-space data using detection models; and a model training module, configured to train the detection models based on training data. Hence, the MRI scan time and related cost are reduced, and the accuracy of the detecting results is increased.

18 Claims, 10 Drawing Sheets

(51) Int. Cl.
    *G01R 33/56*   (2006.01)
    *G16H 30/40*   (2018.01)
    *G16H 50/20*   (2018.01)

(52) U.S. Cl.
    CPC ............. *G16H 30/40* (2018.01); *G16H 50/20* (2018.01); *G06T 2200/04* (2013.01); *G06T 2207/10088* (2013.01); *G06T 2207/20081* (2013.01); *G06T 2207/20084* (2013.01); *G06T 2207/20221* (2013.01)

(58) Field of Classification Search
    CPC ........... G06T 2207/20084; G06T 2207/20221; G01R 33/4836; G01R 33/56; G01R 33/561; G01R 33/5608; G16H 30/40; G16H 50/20; G16H 50/70; A61B 5/055
    See application file for complete search history.

(56) References Cited

U.S. PATENT DOCUMENTS

| | | | |
|---|---|---|---|
| 2019/0056470 A1* | 2/2019 | Wang | G01R 33/5601 |
| 2020/0129784 A1* | 4/2020 | Bériault | G06N 3/08 |
| 2020/0138382 A1* | 5/2020 | Cao | G06T 7/0014 |
| 2020/0402204 A1* | 12/2020 | Huang | G06T 11/003 |
| 2021/0174501 A1* | 6/2021 | Takeshima | G06T 5/50 |

\* cited by examiner

SYSTEM AND METHOD TO DETECT ABNORMALITY OF SUBJECTS DIRECTLY FROM MRI K-SPACE DATA

CROSS REFERENCE TO RELATED APPLICATIONS

This application claims priority to U.S. Provisional Application No. U.S. 63/107,458, filed Oct. 30, 2020, which is hereby incorporated by reference herein as if set forth in its entirety.

BACKGROUND

1. Technical Field

The present disclosure relates to data processing technology, and particularly to a system to detect abnormality of subjects directly from Mill k-space data, and a method to detect abnormality of subjects directly from MRI k-space data.

2. Description of Related Art

Magnetic resonance imaging (MRI) is a non-invasive imaging method to visualize the tissue structures and properties in human bodies. Conventionally, MRI images are firstly acquired using MRI scanners from the person being scanned (subject), then read by radiologists to determine whether there exists abnormalities, such as injuries, stroke, and tumors. This process, however, can be time-consuming and costly, because (a) it takes long scan time to form complete sets of MRI images that has sufficient quality for radiologists to read, and (b) additional time is need for radiologists to read and draw conclusions from the images.

In MRI, the acquired raw data are not data for image pixels but data for k-space (i.e., frequency space), which are the 2D or 3D Fourier domain representation of the images. K-space data, if fully sampled, can be transformed to images by inverse Fourier transform. Some methods have attempted to reduce MRI scan time by partially acquiring k-space and using reconstruction models such as parallel imaging methods (e.g., SENSE, GRAPPA and multiband), and compressed sensing to recover the images. However, these methods introduce noise and artifacts that are increasingly obvious when k-space samples become very sparse. Practically, to form clinically usable MRI images, their maximum acceleration factors are limited to 2 to 8, which still significantly limit the MRI speed.

On the other hand, other methods have attempted to use machine learning to detect abnormalities from MRI images, with lesser or no requirement for radiologists to intervene. However, these methods are designed to take inputs from high-quality images similar to those presented to human radiologists. However, such machine learning approach to abnormality detection requires the formation of complete and quality images, which incurs long MRI scan time. Future, in presence of significant noise and artifacts, it detection accuracies may greatly reduce, if not fail completely at all.

BRIEF DESCRIPTION OF THE DRAWINGS

To describe the technical schemes in the embodiments of the present disclosure or in the prior art more clearly, the following briefly introduces the drawings required for describing the embodiments or the prior art. It should be understood that, the drawings in the following description merely show some embodiments of the present disclosure. For those skilled in the art, other drawings can be obtained according to the drawings without creative efforts.

DETAILED DESCRIPTION

In the following descriptions, for purposes of explanation instead of limitation, specific details such as particular system architecture and technique are set forth in order to provide a thorough understanding of embodiments of the present disclosure. However, it will be apparent to those skilled in the art that the present disclosure may be implemented in other embodiments that are less specific of these details. In other instances, detailed descriptions of well-known systems, devices, circuits, and methods are omitted so as not to obscure the description of the present disclosure with unnecessary detail.

For the purpose of describing the technical solutions of the present disclosure, the following describes through specific embodiments.

Figure 1:
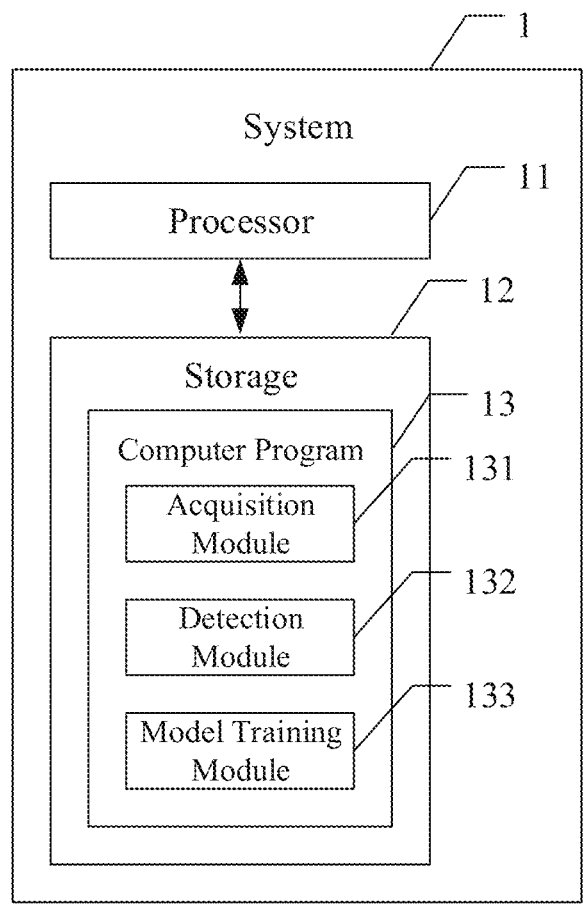
FIG. 1 is a schematic block diagram of a system to detect abnormality of subjects directly from MRI k-space data according to an embodiment of the present disclosure.

FIG. 1 is a schematic block diagram of a system to detect abnormality of subjects directly from MRI k-space data according to an embodiment of the present disclosure. The system 1 to detect abnormality of subjects directly from MRI k-space data without form images is provided, which corresponds to a computer-implemented method to detect abnormality of subjects directly from MRI k-space data described in the following embodiments shown in FIG. 3-FIG. 8. In the embodiments, the term MRI is equivalent to term magnetic resonance (MR).

As shown in FIG. 1, the system 1 includes at least one computer hardware processor 11, at least one non-transitory computer-readable storage medium 12, and at least one computer program 13 stored in the at least one non-transitory computer-readable storage medium 12 and executable on the at least one computer hardware processor 11. When executing (instructions in) the at least one computer program 13, the at least one computer hardware processor 11 implements the method to detect abnormality of subjects directly from MRI k-space data described in the following embodiments shown in FIG. 3-FIG. 8.

Exemplarily, the at least one computer program 13 may be divided into one or more modules/units, and the one or more modules/units are stored in the at least one non-transitory computer-readable storage medium 12 and executed by the at least one computer hardware processor 11 to realize the present disclosure. The one or more modules/units may be a series of computer program instruction sections capable of performing a specific function, and the instruction sections are for describing the execution process of the at least one computer program 13 in the system 1.

The at least one computer program 13 includes an acquisition module 131, a detection module 132, and a model training module 133. The acquisition module 131 is used to obtain target Mill k-space data by scanning a subject, wherein the target MRI k-space data are fully-sampled or undersampled or sparse MRI k-space data. The detection module 132 is used to obtain and output detection outcome from the target MRI k-space data using detection models. The model training module 133 is used to train the detection models based on training data.

In some embodiments, sampling trajectories used in the acquisition module 131 are Cartesian, or radial, or spiral.

In some embodiments, the sampling trajectories used in the acquisition module 131 are optimized for different imaging parts or imaging sections.

In some embodiments, the sampling trajectories used in the acquisition module 131 are optimized for different types of abnormalities.

In some embodiments, the acquisition module 131 is further used to acquire acquisition parameters optimized for different types of abnormalities. The acquisition parameters optimized for different types of abnormalities include, for example, at least one of repetition time (TR), echo time (TE), and bandwidth (BW).

In some embodiments, the target MRI k-space data are obtained from two dimensional (2D) slices, and the detection models can input the MRI k-space data from all of the 2D slices, or perform a slice-wise detection and combine detection results from all of the 2D slices.

In some embodiments, the target MRI k-space data are obtained from a three dimensional (3D) acquisition.

In some embodiments, the detection models are classification models, and output yes or no results. Optionally, the classification models are support vector machines, or decision trees, or artificial neural networks.

In some embodiments, the detection models can be the regression model instead of the classification model, and output a confidence level instead of yes or no results.

In some embodiments, the detection models can be used to characterized abnormalities or pathologies, e.g., location in Cartesian or polar coordinates, size, image intensity deviation, and severity of the abnormalities in terms of sizes and intensity variations, etc.

In some embodiments, the detection models can provide metrics for disease diagnosis, including for staging and screening purposes.

In some embodiments, the training data are obtained from MRI k-space data for training, and the MRI k-space data for training are acquired by actual MRI scanners from normal subjects and abnormal subjects.

In some embodiments, the training data are obtained by simulating k-space data from MRI image datasets of normal subjects and abnormal subjects.

In some embodiments, the training data are obtained by simulating k-space data of normal subjects and abnormal subjects from MRI image datasets of normal subjects.

In some embodiments, the target MRI k-space data are normalized and reordered before input to the detection models.

In some embodiments, the detection models take the target MRI k-space data as input.

In some embodiments, the detection models take the target MRI k-space data and reconstructed images as input.

Figure 2:
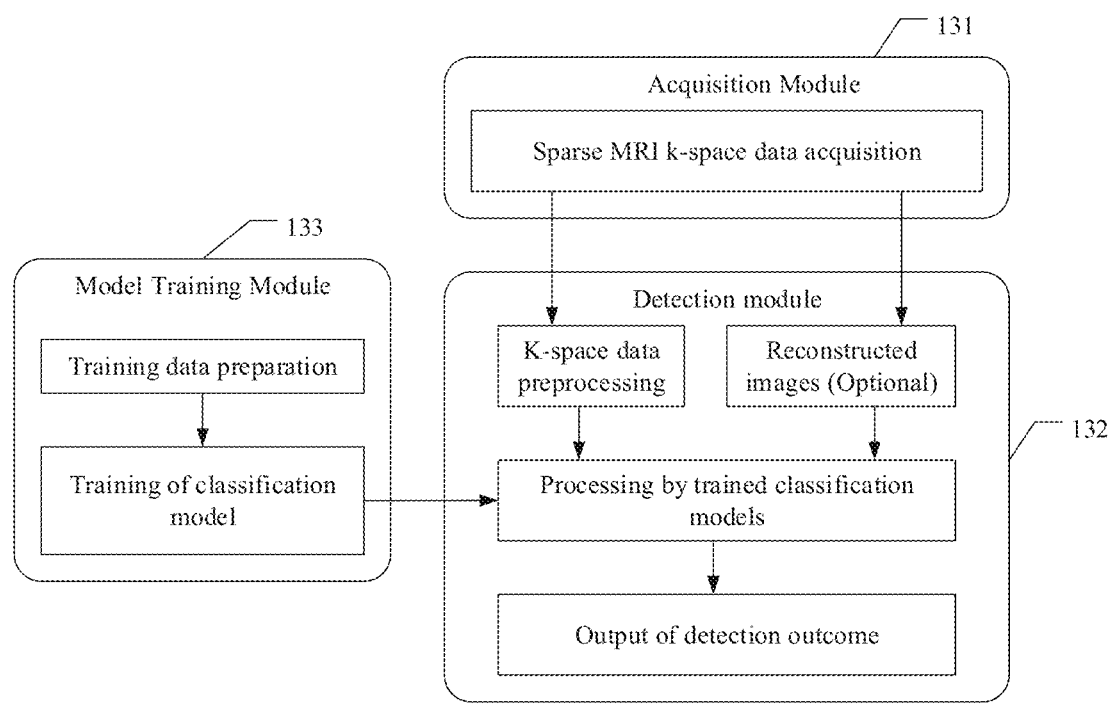
FIG. 2 is a flow chart of abnormality or pathology detection from sparse raw MR k-space data according to an embodiment of the present disclosure.

Specifically, as shown in FIG. 2, in the acquisition module 131, sparse MRI k-space data (that is, the above target MRI k-space data) are acquired from the subject in the region of interest using MRI scanners. The sparse MRI k-space data can be acquired by Cartesian, radial, spiral or other undersampling trajectories. The k-space data are subsequently transferred to the detection module 132 where the k-space data is preprocessed with normalization and reordering, and fed to the trained classification models. Optionally, the sparse MRI k-space data are also reconstructed to images, likely containing substantial artifacts, which are also fed to the trained classification models. The classification models are trained beforehand in the model training module 133, wherein training data with the corresponding labels are prepared and fed to the classification models, iteratively updating the model parameters to minimize the difference between the model output and the labels. The classification models can be support vector machine (SVM), decision trees (e.g., gradient boosting decision tree and random forest), or artificial neural networks (e.g., multi-layer perceptron, convolutional neural network, and recurrent neural network) or combinations of the aforementioned models.

It can be understood by those skilled in the art that FIG. 1 is merely an example of the system 1 and does not constitute a limitation on the system 1, and may include more or fewer components than those shown in the figure, or a combination of some components or different components. For example, the system 1 may further include an input/output device, a network access device, a bus, and the like.

The at least one computer hardware processor 11 may be a central processing unit (CPU), or be other general purpose processor, a digital signal processor (DSP), an application specific integrated circuit (ASIC), a field-programmable gate array (FPGA), or be other programmable logic device, a discrete gate, a transistor logic device, and a discrete hardware component. The general purpose processor may be a microprocessor, or the processor may also be any conventional processor.

The at least one non-transitory computer-readable storage medium 12 may be an internal storage unit of the system 1, for example, a hard disk or a memory of the system 1. The at least one non-transitory computer-readable storage medium 12 may also be an external storage device of the system 1, for example, a plug-in hard disk, a smart media card (SMC), a secure digital (SD) card, flash card, and the like, which is equipped on the system 1. Furthermore, the at least one non-transitory computer-readable storage medium 12 may further include both an internal storage unit and an external storage device, of the system 1. The at least one non-transitory computer-readable storage medium 12 is configured to store the at least one computer program 13 and other programs and data required by the system 1. The at least one non-transitory computer-readable storage medium 12 may also be used to temporarily store data that has been or will be output.

Figure 3:
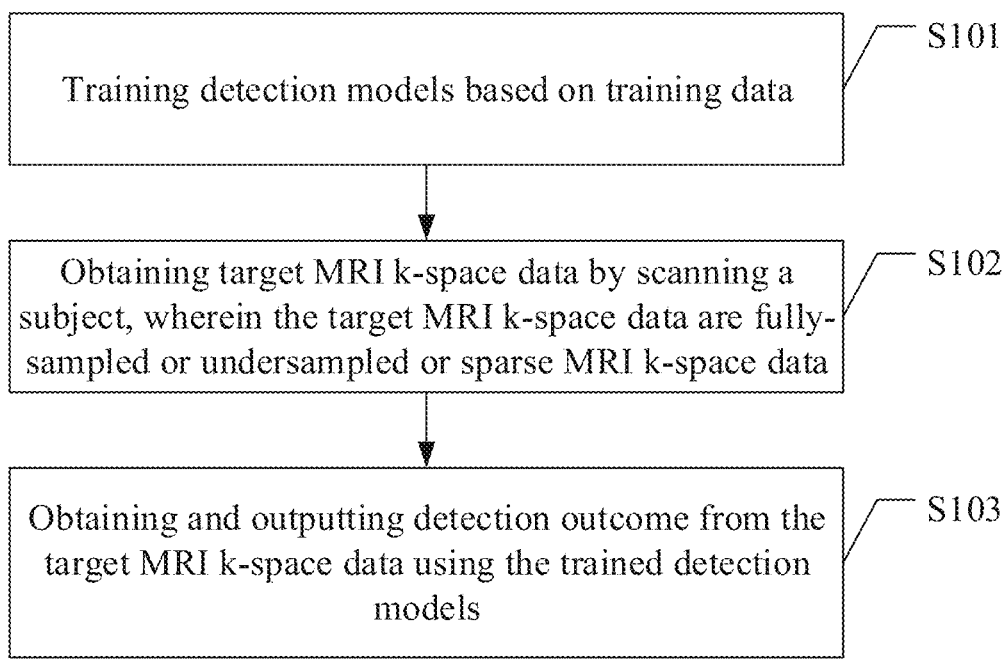
FIG. 3 is a flow chart of a method to detect abnormality of subjects directly from MRI k-space data according to an embodiment of the present disclosure.
Figure 10:
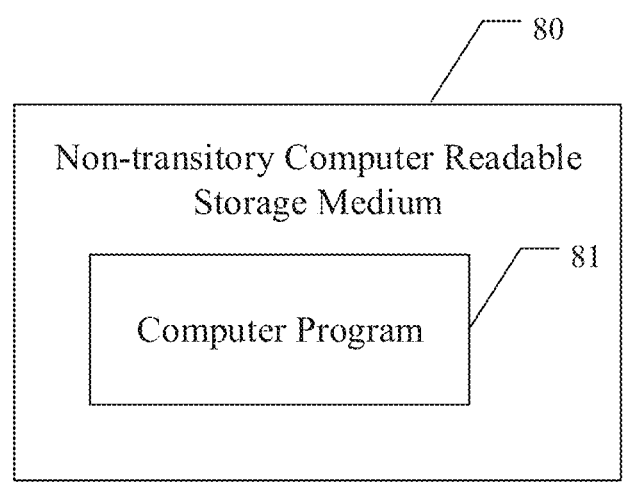
FIG. 10 is a schematic block diagram of a non-transitory computer readable storage medium according to an embodiment of the present disclosure.

FIG. 3 is a flow chart of a method to detect abnormality of subjects directly from MIll k-space data according to an embodiment of the present disclosure. The method is a computer-implemented method executable for a processor, which may be implemented through and applied to the system 1 as shown in FIG. 1 or implemented through a non-transitory computer readable storage medium as shown in FIG. 10. As shown in FIG. 3, in this embodiment, the method includes the following steps.

S101: training detection models based on training data;

S102: obtaining target MRI k-space data by scanning a subject, wherein the target MRI k-space data are fully-sampled or undersampled or sparse MRI k-space data;

S103: obtaining and outputting detection outcome from the target MRI k-space data using the trained detection models.

In some embodiments, the method can incorporate anatomical prior information to enhance the detection performance, specifically, the step S101 includes: obtaining the training data, and dividing the training data into first anatomical sections, wherein the training data include MRI images for training and MRI k-space data for training; and training the detection models on each of the first anatomical sections. The detection models are anatomical specific abnormality detection models.

The method further includes: acquiring scan data of the subject while scanning the subject, identifying second anatomical sections on the scan data, and determining reconstruction models corresponding to the second anatomical sections from the trained detection models; reconstructing and obtaining reconstructed MRI images using the determined reconstruction models on each of the second anatomical sections; and merging the reconstructed MRI images from each of the second anatomical sections, and obtaining the merged MRI image.

The step S103 includes: obtaining and outputting the detection outcome from the target MRI k-space data and the merged MRI image using the trained detection models.

In some embodiments, at least one or any combination of navigator signals, undersampled MRI data, and at least one scout scan is acquired and used to identify the second anatomical sections. For example, the at least one scout scan is acquired to identify the second anatomical sections, or the navigator signals are acquired to identify the second anatomical sections, or the undersampled MRI data can be used to identify the second anatomical sections, or the aforementioned scout scan, navigator signals or undersampled MR data can be combined to identify the second anatomical sections.

In some embodiments, the sampling trajectories of the target MRI k-space data are Cartesian, or radial, or spiral.

In some embodiments, the sampling trajectories of the target MRI k-space data are optimized for different imaging parts or imaging sections.

In some embodiments, the sampling trajectories of the target MRI k-space data are optimized for different types of abnormalities.

In some embodiments, other acquisition parameters are acquired and optimized for different types of abnormalities. The other acquisition parameters include: at least one of TR, TE, and BW.

In some embodiments, the target MRI k-space data are obtained from two dimensional (2D) slices, and the detection models can input the target MRI k-space data from all of the 2D slices, or perform a slice-wise detection and combine detection results from all of the 2D slices.

In some embodiments, the target MRI k-space data are obtained from a three dimensional (3D) acquisition.

In some embodiments, the detection models are classification models, and output yes or no results. Optionally, the classification models are support vector machines, or decision trees, or artificial neural networks.

In some embodiments, the detection models can be the regression model instead of the classification model, and output a confidence level instead of yes or no results.

In some embodiments, the detection models can be used to characterized abnormalities or pathologies, e.g., location in Cartesian or polar coordinates, size, image intensity deviation, and severity of the abnormalities in terms of sizes and intensity variations, etc.

In some embodiments, the detection models can provide metrics for disease diagnosis, including for staging and screening purposes.

In some embodiments, the training data are obtained from MRI k-space data for training, and the MRI k-space data for training are acquired by actual MRI scanners from normal subjects and abnormal subjects.

In some embodiments, the training data are obtained by simulating k-space data from MRI image datasets of normal subjects and abnormal subjects.

In some embodiments, the training data are obtained by simulating k-space data of normal subjects and abnormal subjects from MRI image datasets of normal subjects.

In some embodiments, the target MRI k-space data are normalized and reordered before input to the detection models.

In some embodiments, the detection models take the target MRI k-space data as input.

In some embodiments, the detection models take the target MRI k-space data and reconstructed images as input.

Figure 4:
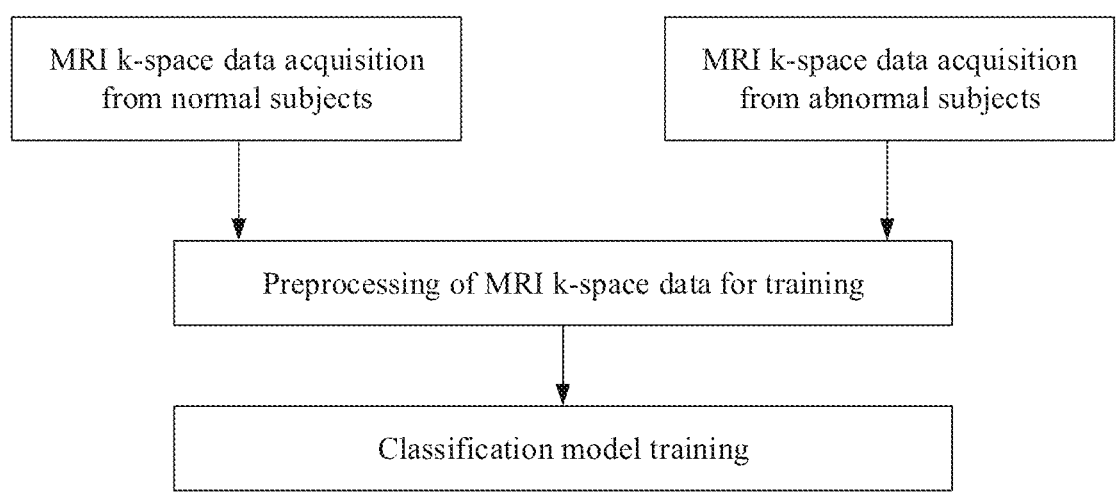
FIG. 4 is a flow chart of training detection models in FIG. 3.

The following will be described in detail in connection with FIG. 4 to FIG. 8. FIG. 4 shows the procedure of training the detection models in some embodiments. As shown in FIG. 4, the MRI k-space data for training are acquired by actual MRI scanners from normal subjects and abnormal subjects, processed including normalization and ordering, and fed to the classification models.

Figure 5:
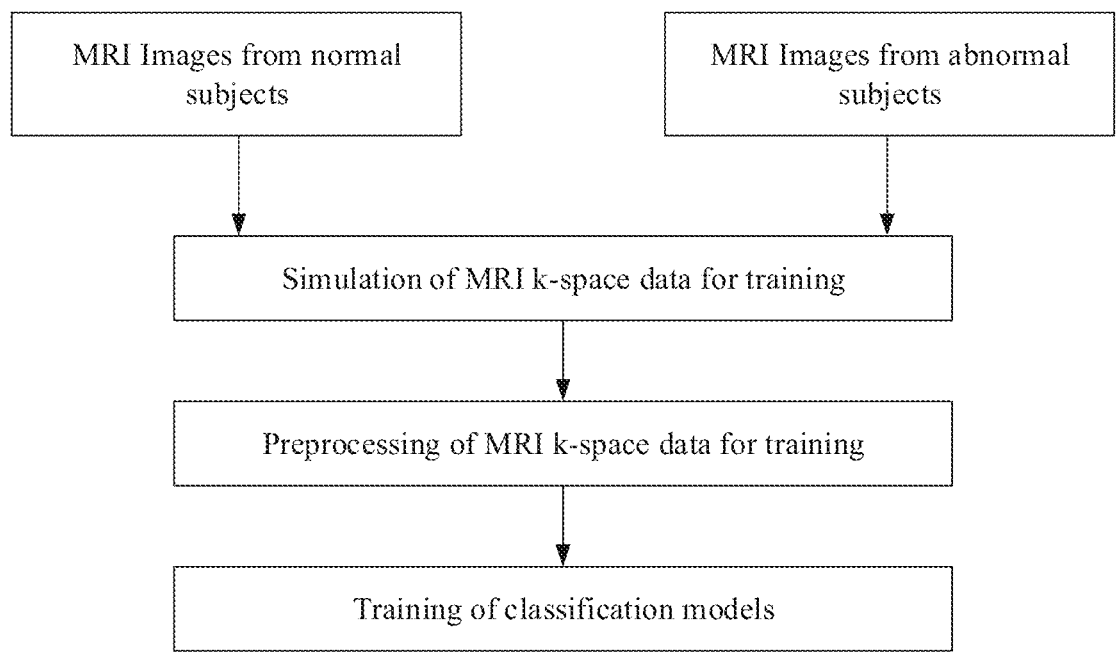
FIG. 5 is a flow chart of procedures of the training detection models in FIG. 3 with MRI images from normal subjects and abnormal subjects.
Figure 6:
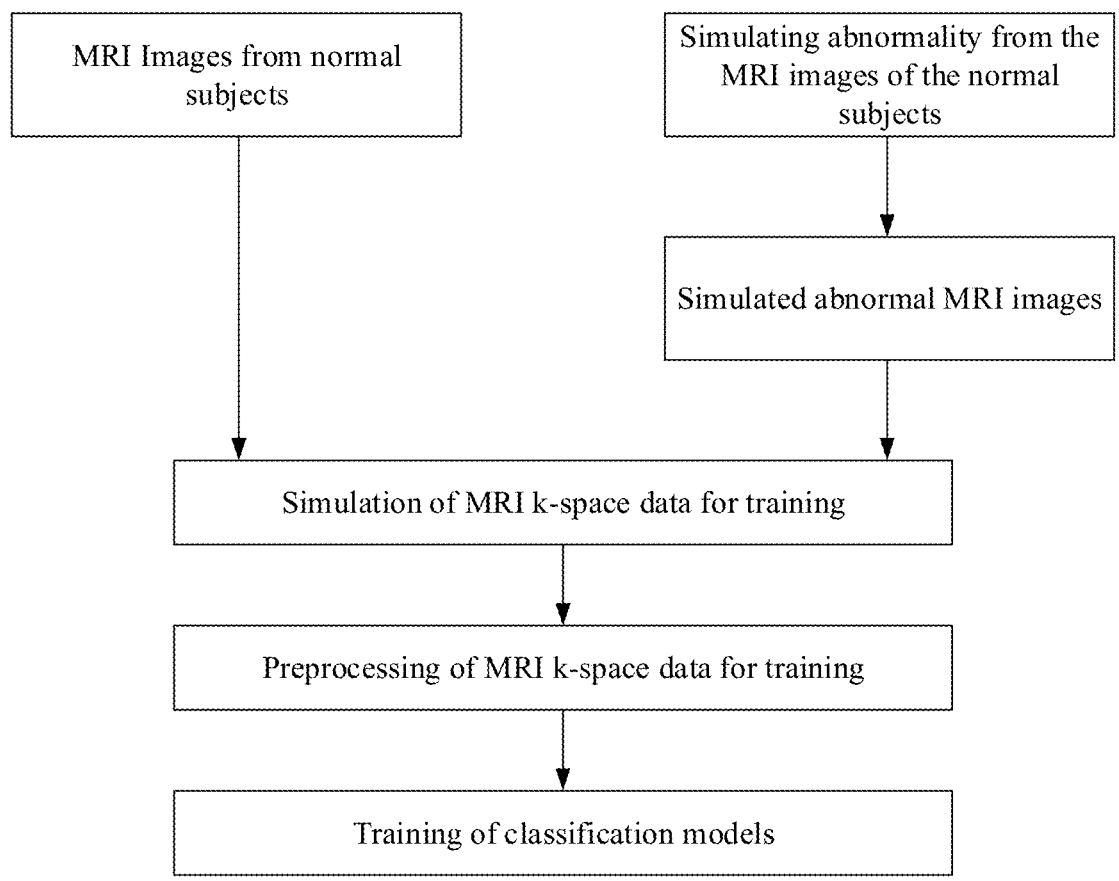
FIG. 6 is a flow chart of procedures of the training detection models in FIG. 3 with MRI images from normal subjects and simulated abnormalities.

FIG. 5 shows the procedure of training the detection models in some other embodiments. As shown in FIG. 5, the MIll k-space data for training are simulated from MRI images datasets from the normal subjects and the abnormal subjects and gone through similar steps in FIG. 4. FIG. 6 shows the procedure of training the models in still some other embodiments, wherein the only the MRI images of the normal subjects are available and MRI images of the abnormal subjects are simulated from the MRI images of the normal subjects, and gone through similar steps in FIG. 5.

Figure 7:
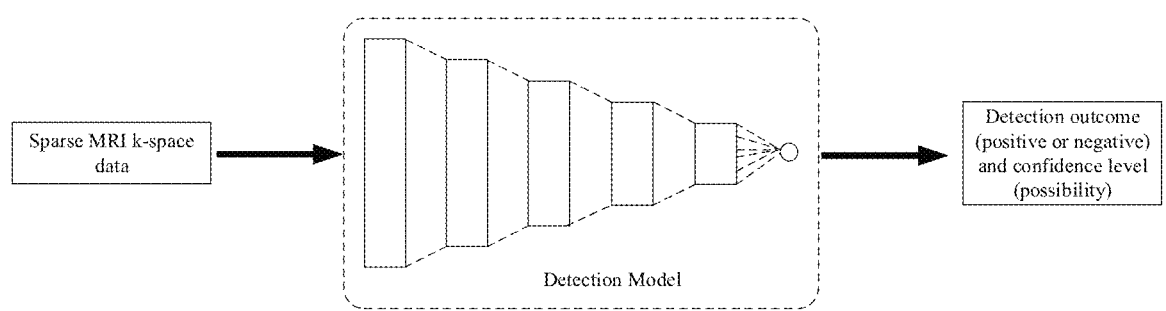
FIG. 7 is a flow chart of a method to detect the abnormality from k-space data according to an embodiment of the present disclosure.
Figure 8:
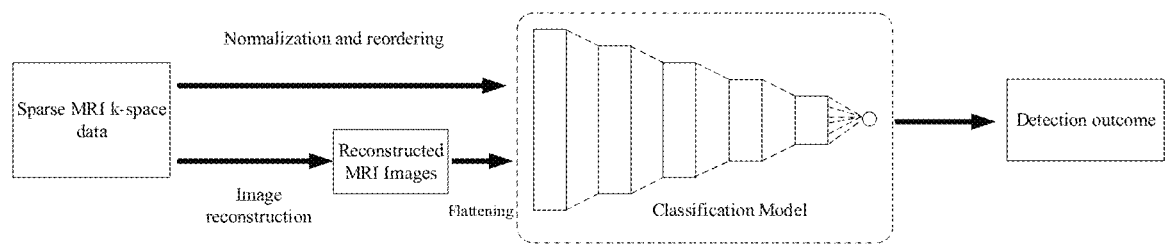
FIG. 8 is a flow chart of a method to detect the abnormality from k-space data and reconstructed images according to an embodiment of the present disclosure.

FIG. 7 illustrates the operation of the classification models to detect the abnormality from the k-space data in some embodiments. The sparse MIll k-space data (that is, the above target MRI k-space data) are normalized, reordered, and input to the detection models (e.g., classification models, such as fully-connected multiplayer perceptron (MLP)), which subsequently outputs the detection outcome with scores indicating the confidence level (i.e., possibilities). FIG. 8 shows the operation of the classification models to detect the abnormality from the k-space data in some other embodiments, in addition to the sparse MRI k-space data (that is, the above target MIll k-space data), reconstructed images are also input to the classification models (e.g., MLP). The reconstruction can be performed by non-uniform Fourier transform, parallel imaging reconstruction (e.g., SENSE, GRAPPA, SPIRIT), low-rank regularized reconstruction or compressed sensing reconstruction.

Figure 9:
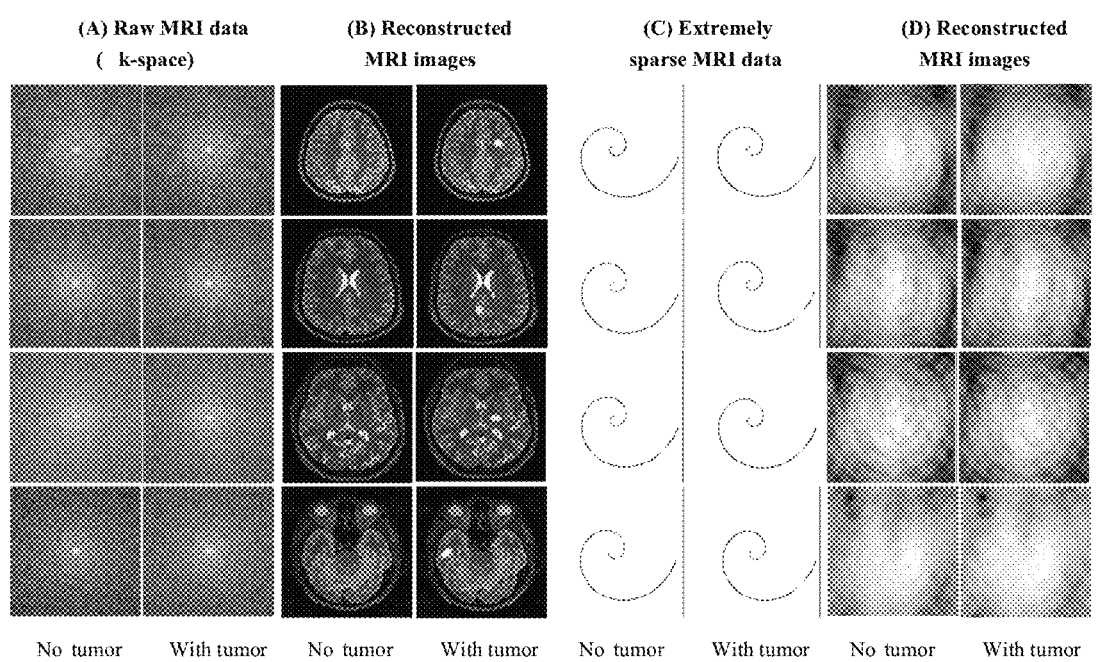
FIG. 9 is a schematic diagram of results of different detection methods including the method of the present disclosure.

As a practical application of the above method, the pathology detection is achieved from extremely sparse MR raw data space (i.e., k-space data) via deep learning from anatomy- and pathology-specific k-space data. In one example, the detect brain tumor is detected directly from the extremely sparse k-space by (i) deep learning of anatomy-specific datasets and (ii) bypassing the traditional MRI image reconstruction procedure prior to pathology diagnosis. As shown in FIG. 9, (A) corresponds to fully sampled raw MRI data in k-space; (B) corresponds to MRI images reconstructed from full k-space data, with right column images containing 5-10 mm hyper-intensity tumors; (C) corresponds to extremely sparse MRI k-space data using single-shot spiral acquisition; (D) corresponds to MRI images reconstructed from single-shot spiral (unusable for pathology detection). The preliminary simulation results here demonstrate that the image-free detection strategy of the present disclosure can yield 97.3% sensitivity and 98.4% specificity for tumor detection from only 1.5% of the raw MR data.

The above system and the above method can refer to each other.

The present disclosure relates to detecting abnormalities in MRI, specifically to using machine learning classification models to detect abnormalities from MRI k-space data. According to some aspects, highly sparse k-space data are acquired using MRI scanners from the regions of interest of the subject. Unlike previous methods, the steps of reconstructing images are not required, and the classification models are trained on the k-space data to predict of existence of abnormality.

Accordingly, several advantages include: (1) the Mill scan time and related cost are reduced because only relatively small portion of full k-space data is required; (2) the time and related cost for doctors to read the images are saved; (3) the reconstruction time and related cost for transforming k-space data to images is saved, and; (4) the present classification model is robust to achieve high detection accuracy at high acquisition acceleration factors or very short scan time.

FIG. 10 is a schematic block diagram of a non-transitory computer readable storage medium according to an embodiment of the present disclosure. A non-transitory computer readable storage medium 80 is provided, which corresponds to the method for Mill reconstruction or/and the method for MRI data acquisition described in the above-mentioned embodiments. As shown in FIG. 10, the non-transitory computer readable storage medium 80 is configured to store a computer program 81. When the computer program 81 is executed by a processor, the method to detect abnormality of subjects directly from Mill k-space data in the above-mentioned embodiments is implemented. The computer program 81 further includes instructions for implementing the above acquisition module 131, the detection module 132, and the model training module 133.

The non-transitory computer readable storage medium 80 can be a server, a U disk, a mobile hard disk, a read-only memory (ROM), a random access memory (RAM), a magnetic disk, an optical disk, or other medium that can store program codes.

In the embodiments provided by the present disclosure, it should be understood that the disclosed method, system, and apparatus (or device) may be implemented in other manners. For example, the above-mentioned system and apparatus embodiment is merely exemplary. For example, the division of modules or units is merely a logical functional division, and other division manner may be used in actual implementations, that is, multiple units or components may be combined or be integrated into another system, or some of the features may be ignored or not performed.

The units described as separate components may or may not be physically separated. The components represented as units may or may not be physical units, that is, may be located in one place or be distributed to multiple network units. Some or all of the units may be selected according to actual needs to achieve the objectives of this embodiment.

In addition, each of the functional units or modules in each of the embodiments of the present disclosure can be integrated in one processing unit. Each unit or modules can be physically exists alone, or two or more units can be integrated in one unit, or two or more modules can be integrated in one module. The above-mentioned integrated unit or module can be implemented either in the form of hardware, or in the form of software functional units or modules.

The integrated unit or module can be stored in a computer-readable storage medium if it is implemented in the form of a software functional unit and sold or utilized as a separate product. Based on this understanding, the technical solution of the present disclosure, either essentially or in part, contributes to the prior art, or all or a part of the technical solution can be embodied in the form of a software product. The software product is stored in a storage medium, which includes a number of instructions for enabling a computer device (which can be a personal computer, a server, a network device, etc.) or a processor to execute all or a part of the steps of the methods described in each of the embodiments of the present disclosure. The above-mentioned storage medium includes a variety of media such as a USB disk, a mobile hard disk, a read-only memory (ROM), a random access memory (RAM), a magnetic disk, and an optical disk which is capable of storing program codes.

As mentioned above, the forgoing embodiments are merely intended for describing but not for limiting the technical schemes of the present disclosure. Although the present disclosure is described in detail with reference to the above-mentioned embodiments, it should be understood by those skilled in the art that, the technical schemes in each of the above-mentioned embodiments may still be modified, or some of the technical features may be equivalently replaced, while these modifications or replacements do not make the essence of the corresponding technical schemes depart from the spirit and scope of the technical schemes of each of the embodiments of the present disclosure, and should be included within the scope of the present disclosure.

What is claimed is:

1. A system to detect abnormality of subjects directly from magnetic resonance imaging (MRI) k-space data, comprising:
   at least one computer hardware processor;
   at least one non-transitory computer-readable storage medium; and
   at least one computer program stored in the at least one non-transitory computer-readable storage medium and executable on the at least one computer hardware processor, wherein the at least one computer program comprises:
   an acquisition module, configured to obtain target MRI k-space data by scanning a subject, wherein the target MRI k-space data are fully-sampled or undersampled or sparse MRI k-space data;

a detection module, configured to obtain and output detection outcome from the target MRI k-space data using detection models; and a model training module, configured to train the detection models based on training data;

wherein the training data are obtained by simulating k-space data from MRI image datasets of normal subjects and abnormal subjects, or wherein the training data are obtained by simulating k-space data of normal subjects and abnormal subjects from MRI image datasets of normal subjects.

2. The system of claim 1, wherein sampling trajectories used in the acquisition module are Cartesian, or radial, or spiral.

3. The system of claim 2, wherein the sampling trajectories are optimized for different imaging parts or imaging sections; or the sampling trajectories are optimized for different types of abnormalities.

4. The system of claim 1, wherein the acquisition module is further configured to acquire acquisition parameters optimized for different types of abnormalities.

5. The system of claim 4, wherein the acquisition parameters optimized for different types of abnormalities comprise at least one of repetition time, echo time, and bandwidth.

6. The system of claim 1, wherein the target MRI k-space data are obtained from two dimensional (2D) slices, and the detection models input the target MRI k-space data from all of the 2D slices, or perform a slice-wise detection and combine detection results from all of the 2D slices; or the target MRI k-space data are obtained from a three dimensional (3D) acquisition.

7. The system of claim 1, wherein the detection models are classification models, and output yes or no results.

8. The system of claim 7, wherein the classification models are support vector machines, or decision trees, or artificial neural networks.

9. The system of claim 1, wherein the detection models are regression models, and output a confidence level.

10. The system of claim 1, wherein the detection models are configured to characterized abnormalities or pathologies.

11. The system of claim 10, wherein the abnormalities or pathologies comprise: location in Cartesian or polar coordinates, size, image intensity deviation, and severity of the abnormalities in terms of sizes and intensity variations.

12. The system of claim 1, wherein the detection models provide metrics for staging and screening purposes.

13. The system of claim 1, wherein the target MRI k-space data are normalized and reordered before input to the detection models.

14. The system of claim 1, wherein the detection models take the target MRI k-space data as input.

15. The system of claim 1, wherein the detection models take the target MRI k-space data and reconstructed images as input.

16. A computer-implemented method to detect abnormality of subjects directly from magnetic resonance imaging (MRI) k-space data, comprising executing on a processor with steps of:

training detection models based on training data;

obtaining target MRI k-space data by scanning a subject, wherein the target MRI k-space data are fully-sampled or undersampled or sparse MRI k-space data;

obtaining and outputting detection outcome from the target MRI k-space data using the trained detection models;

wherein the training data are obtained by simulating k-space data from MRI image datasets of normal subjects and abnormal subjects, or wherein the training data are obtained by simulating k-space data of normal subjects and abnormal subjects from MRI image datasets of normal subjects.

17. The method of claim 16, wherein the step of training the detection models based on training data comprises:

obtaining the training data, and dividing the training data into first anatomical sections, wherein the training data comprise MRI images for training and MRI k-space data for training; and training the detection models on each of the first anatomical sections;

wherein method further comprises:

acquiring scan data of the subject while scanning the subject, identifying second anatomical sections on the scan data, and determining reconstruction models corresponding to the second anatomical sections from the trained detection models;

reconstructing and obtaining reconstructed MRI images using the determined reconstruction models on each of the second anatomical sections; and merging the reconstructed MRI images from each of the second anatomical sections, and obtaining merged MRI image; and wherein the step of obtaining and outputting detection outcome from the target MRI k-space data using the trained detection models comprises:

obtaining and outputting the detection outcome from the target MRI k-space data and the merged MRI image using the trained detection models.

18. The method of claim 17, wherein at least one or any combination of navigator signals, undersampled MRI data, and at least one scout scan is acquired and used to identify the second anatomical sections.

* * * * *